(12) United States Patent
Orts et al.

(10) Patent No.: US 6,992,064 B2
(45) Date of Patent: Jan. 31, 2006

(54) N-ALKYLGLYCINE TRIMERES CAPABLE OF PROTECTING NEURONS AGAINST EXCITOTOXIC AGGRESSIONS AND COMPOSITIONS CONTAINING SUCH TRIMERES

(75) Inventors: Vicente Felipo Orts, Valencia (ES); Carmen Montoliu Felix, Valencia (ES); Antonio Ferrer Montiel, Barcelona (ES); Rosa Planells Cases, Barcelona (ES); Jaime M. Merino Fernandez, Barcelona (ES); Enrique Perez Paya, Barcelona (ES); Francisco Sanchez Baeza, Barcelona (ES); Merc Humet, Barcelona (ES); Angel Messeguer Peypoch, Barcelona (ES)

(73) Assignee: Diverdrugs, S.L., Gavá (ES)

( * ) Notice: Subject to any disclaimer, the term of this patent is extended or adjusted under 35 U.S.C. 154(b) by 0 days.

(21) Appl. No.: 10/398,467

(22) PCT Filed: Oct. 5, 2001

(86) PCT No.: PCT/ES01/00369

§ 371 (c)(1),
(2), (4) Date: Aug. 21, 2003

(87) PCT Pub. No.: WO02/28885

PCT Pub. Date: Apr. 11, 2002

(65) Prior Publication Data

US 2004/0029811 A1 Feb. 12, 2004

(30) Foreign Application Priority Data

Oct. 6, 2000 (ES) ............................... 200002414

(51) Int. Cl.
*A61K 38/06* (2006.01)
*C07K 5/083* (2006.01)
(52) U.S. Cl. ....................................... 514/18; 530/331
(58) Field of Classification Search ................... 514/18; 530/331
See application file for complete search history.

(56) References Cited

U.S. PATENT DOCUMENTS 6,124,361 A * 9/2000 Chenard ...................... 514/561
6,384,069 B1 * 5/2002 Feuerstein et al. ........... 514/409
6,391,871 B1 * 5/2002 Olney et al. ............ 514/214.01

FOREIGN PATENT DOCUMENTS

WO WO 96/40747 A * 12/1996

OTHER PUBLICATIONS

Gibbons et al. Pharmacologic characterization of CHIR 2279 . . . Journal of Pharmacology and Experimental Therapeutics. 1996, vol. 277, No. 2, pp. 885-889.*
Goodson et al Characterization of novel antimicrobial peptoides. Antimicrobial Agents and Chemotherapy. 1999, vol. 43, No. 6, pp. 1429-1434.*
Kirshenbaum et al. Sequence specific polypeptoids . . . Proceedings of the National Academy of Science USA. Apr. 14, 1998, vol. 95, No. 8, pp. 4303-4308.*
Wu et al. Peptoid Oligomers with alpha-Chiral Aromatic Side Chains . . . Journal of the American Chemical Society. 2001, vol. 123, pp. 2958-2963.*
Zuckermann et al. Discovery of nanomolar ligands . . . Journal of Medicinal Chemistry. 1994, vol. 37, pp. 2678-2685.*

* cited by examiner

*Primary Examiner*—Jeffrey Edwin Russel
(74) *Attorney, Agent, or Firm*—Kirkpatrick & Lockhart Nicholson Graham LLP; Anthony H. Handal

(57) ABSTRACT

N-alkylglycine trimeres, their stereoisomers, racemic mixtures and salts of formula (I) below, where $R_1$, $R_2$ and $R_3$, independent of one another, are chosen from amongst cyclopropyl, sec-butyl, 2-methoxyethyl, 3-methylbutyl, cyclohexyl, 2-(N-pyrrolidinyl)ethyl, 2-(methylcarbonylamine) ethyl, 3-(2-oxo-N-pyrrolidinyl)propyl, 2-(2-pyridyl)ethyl, 2-phenylethyl, 1-(2-tetrahydrofuryl)methyl, 2-(N-imidazolyl) ethyl, 2-(4-methoxyphenyl)ethyl, 2-(3,4-dimethoxyphenyl)ethyl, 2-(2,4-dichlorophenyl)ethyl, 2-[2-(N-methyl)pyrrolidinyl]ethyl, 2-(4-aminosulfonylphenyl)ethyl, 2-(morpholine)ethyl, 3-(N,N-diethylamine)propyl, 3,3-diphenyipropyl, 3-(N,N-dimethylamine)propyl, and 2-(N,N-diethylamine)ethyl, their stereoisomeric forms and their mixtures, which are capable of blocking L-glutamate receptors and are useful for treating disorders mediated by neurodegeneration, for example, cerebral ischemia, cerebrovascular accident, migraine, depression, Huntington, Parkinson, Alzheimer, senile dementia, epilepsy and multiple and amyotrophic sclerosis.

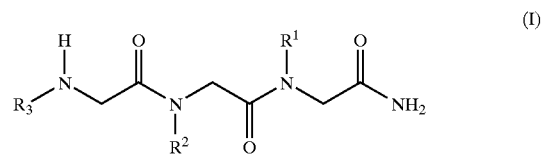

(I)

11 Claims, No Drawings

N-ALKYLGLYCINE TRIMERES CAPABLE OF PROTECTING NEURONS AGAINST EXCITOTOXIC AGGRESSIONS AND COMPOSITIONS CONTAINING SUCH TRIMERES

SCOPE OF THE INVENTION

This invention refers to N-alkylglycine trimeres capable of protecting neurones against excitotoxic aggressions, useful as neuroprotectors, to compositions containing them and to their employment in the treatment of illnesses or disorders mediated by the excitotoxicity.

BACKGROUND OF THE INVENTION

Neurodegenerative illnesses and neurological disorders constitute a serious social and economic problem. Clear examples are represented by senile dementia, Alzheimer, Huntington, and the one associated to the AIDS virus, as well as the neurodegeneration caused by ischemia associated to a cerebrovascular accident. In spite of the seriousness of the problem, the pharmacological arsenal to fight, prevent, and/or decrease its symptoms and progress, is surprisingly limited.

Though the biological mechanisms that lead to the neurodegeneration are not clearly established, in many neurodegenerative illnesses, such as amiotrophic lateral sclerosis, dementia associated to AIDS and to Alzheimer, the presence of high and chronic levels of the L-glutamate excitotoxic neurotransmitter (1–3), has been observed in the cerebral parenchyma. This neurotransmitter has also been involved in the etiology of neurological disorders such as cerebral ischemia (4). The glutamate activates membrane receptors that have an ionic channel activity (ionotropic receptors) or that transduce the signal through G proteins (metabotropic receptors) (5). The ionotropic receptors, especially those of the NNDA type [N-methyl-D-aspartate activated glutamate receptors (NMDA)], have been involved in the glutamatergic neurodegeneration due to their high $Ca^{2+}$ ion permeability (1–5). The proposed molecular mechanism indicates that high and chronic levels of glutamate cause a prolonged activation (hyperactivation) of the NMDA receptor that "overloads" the neurones with $Ca^{2+}$ ions, triggering off the massive activation and excessive intracellular cascades that, inevitably lead to neuronal death (1–8). In fact, it has been described that antagonists of this receptor are capable of preventing the glutamate neurotoxicity (8,9). From what is expounded it can be deduced, that a strategy for preventing or decreasing the neurodegeneration is to control the functional activity of this ionotropic receptor, especially, under conditions in which a high pathology of the glutamate levels exist.

In spite of the advance made in the past few years, potent, selective and toxicity-free neuroprotectors have not yet been developed. Up to the moment, a large part of the effort has been focused, towards the development of competitive inhibitors that recognise the glutamaterglcal receptors of the central nervous system (1,2). For example, an important effort has been made to develop competitive and non competitive antagonists of glutamate and/or glycine [a coagonist that participates in the activation of the NMDA type glutamate]. These molecules, though powerful neuroprotectors, present important secondary effects, such as cognitive anomalies, that limit their clinical use (10–12). The main disadvantage of using competitive and non competitive antagonist is that they interact with their receptors, non specifically inhibiting the neurotransmission, and affecting both the pathological activity of the glutamate and its physiological activity (13). A strategy to overcome this therapeutic obstacle would be to use non competitive and/or acompetitive antagonists that preferably join the agonists-receptor complex. The most important advantage of using this type of antagonists is that these agents mainly act on hyperactivated receptors (pathological receptors), showing a marginal interaction over receptors that perform on rapid excitory neurotransmission processes (physiological receptors) (13). This preferred activity over the "pathological" receptors makes these types of antagonists valued as promising therapeutic agents to prevent the neurodeceneration (13–18). Molecules such as phencyclidine and dizolcipine are powerful acompetitive antagonists of the NMDA receptor that act as efficient in vitro neuroprotectors (12–18). However, their clinical use is questioned due to the psycotomimetic effects (13).

SUMMARY OF THE INVENTION

The invention faces the problem of searching for new neuroprotector compounds capable of preventing, decreasing or treating neurodegeneration, preferably, the excitotoxic, that overcome totally or partly the previously indicated disadvantages.

The solution provided by this invention is based on the development of N-alkylglycine trimeres that are capable of blocking the ionotropic glutamate receptors and that may be used to prevent, decrease or treat neurodegeneration, as well as prevent or treat illnesses or disorders mediated by the neurodegeneration. The capacity of said N-alkylglycine trimeres for blocking the NMDA type glutamate ionotropic receptors as well as their capacity to prevent excitotoxic neuronal death caused by a prolonged exposure to L-glutamic in the absence or presence of glycine, has been shown by means of the tests described in Example 1.2.

Consequently, an object of this invention is constituted by N-alkylglycine trimeres capable of blocking the glutamate ionotropic receptors, useful for blocking the excitotoxic aggressions response.

An additional object of this invention is constituted by a composition that comprises at least one of said N-alkylglycine trimeres, such as a pharmaceutical composition.

The employment of said N-alkyiglycine trimeres in the elaboration of a medicine for the prevention or treatment of illnesses or disorders mediated by the neurodegeneration constitutes another additional object of this invention.

DETAILED DESCRIPTION OF THE INVENTION

The invention provides general formula (I) N-alkylglycine trimeres

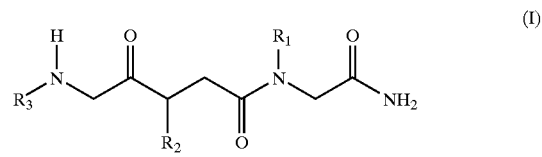

where, $R_1$, $R_2$ and $R_3$, equal or different, independent of one another, are chosen from amongst cyclopropyl, sec-butyl, 2-methoxyethyl, 3-methylbutyl, cyclohexyl, 2-(N-pyrrolidinyl) ethyl, 2-(methylcarbonylamine)ethyl, 3-(2-oxo-N-pyrrolydinyl)propyl, 2-(2-pyridyl)ethyl, 2-phenylethyl, 1-(2-tetrahydrofuryl)methyl, 2-(N-imidzolyl)ethyl, 2-(4-metoxyphenyl)ethyl, 2-(3,4-dimetoxyphenyl)ethyl, 2-(2, 4-dichlorophenyl)ethyl, 2-[2-(N-methyl)pyrrolidinyl] ethyl, 2-(4-aminosulfonylphenyl)ethyl, 2-(morpholine) ethyl, 3-(N,N-diethylamine)propyl, 3,3-diphenylpropyl, 3-(N,N-dimethylamine)propyl and 2-(N,N-diethylamine) ethyl, their stereoisomeric forms and mixtures, racemic or non racemic, of the same, and their pharmaceutically acceptable salts.

Some formula (I) N-alkylglycine trimeres may have one or more chiral centres. Consequently, said formula (I) compounds may exist under any of their stereoisomeric forms (enantiomeric or diastereoisomeric) or in mixtures, racemic or non racemic, of the same, all of which fall within the scope of the present invention. Illustrative examples of formula (I) N-alkylglycine trimeres that contain chiral centres include those that contain sec-butyl groups [(R,S)-sec-butyl, (R)-sec-butyl or (S)-sec-butyl]; 1-(2-tetrahydrofuryl) methyl [(R,S)-1-(2-tetrahydro-furyl)methyl, (R)-1-(2-tetrahydrofuryl)methyl or (S)-1-(2-tetra-hydrofuryl) methyl]; or 2-[2-(N-methyl)pyrrolidinyl]ethyl, [(R,S)-2-[2-(N-methyl)pyrrolidinyl]ethyl, (R)-2-[2-(N-methyl) pyrrolidinyl] ethyl or (S)-2-[2-(N-methyl)pyrrolidinyl]ethyl].

In a particular embodiment, the invention provides formula (I) N-alkylglycine trimeres in which the $R_1$ is sec-butyl, 2-phenylethyl, N-acetamidoethyl, N,N-dimethylaminopropyl, or 2-(N-imidazolyl)ethyl, and their stereocoisomeric forms and mixtures, racemic or non racemic, of the same.

In another particular embodiment, the invention provides formula (I) N-alkylglycine trimeres in which $R_2$ is cyclopropyl, N,N-diethylaminopropyl, 2-(morpholine)ethyl or 3,3-diphenylpropyl and their stereoisomeric forms and mixtures, racemic or non racemic, of the same.

In another particular embodiment, the invention provides formula (I) N-alkylglycine trimeres in which $R_3$ is 2-(N-pyrrolidyl)ethyl, cyclopropyl, 3,3-diphenylpropyl or N-methylpyrroidyl-2-ethyl, and their stereoisomeric forms and mixtures, racemic or non racemic, of the same.

In another particular embodiment, the invention provides an N-alkylglycine trimere that additionally contains a reversible modification with the purpose of increasing its bioavailability and ease of passage of the hematoencephalic barrier and epitelial tissue.

Illustrative examples of formula (I) N-alkylglycine trimeres provided by this invention are gathered in Table 1 [Example 1.1].

Within the scope of this invention, are to be found, the pharmaceutically acceptable salts of the formula (I) N-alkylglycine trimeres provided by this invention. The term "pharmaceutically acceptable salts" includes the salts normally used to form metallic salts or salts with acid additives. The nature of the salt is not critical, provided it is pharmaceutically acceptable. The pharmaceutically acceptable salts of formula (I) N-alkylglycine trimeres may be obtained as from acids, organic or inorganic. Said salts may be obtained by conventional techniques, well known to experts in the art, reacting the appropriate acid with the formula (I) N-alkylglycine trimeres.

Formula (I) N-alkylglycine trimeres can be obtained by conventional methods, for example, by means of copulation and amidation reactions, among the glycine derivates that constitute the structural components of said trimeres. The glycine derivates can in turn be obtained by means of conventional methods of amino acid modification. The stereosiomeric forms of the formula (I) N-alkylglycine trimeres can be synthesised as from the corresponding enantiomerics or from racemic or non racemic mixtures of the raw products. When parting from enantiomeric mixtures, the obtained stereoisomerics can be separated by conventional methods of stereoisomeric resolution (enantiomerics and diastereoisomerics), for example, fractionized crystallisation; chromatography or salts formation.

Formula (I) N-alkylglycine trimeres are capable of blocking the glutamate ionotropic receptors and can be used to prevent, decrease or treat neurodegeneration, preferably, the neurodegeneration by excitoxicity, as well as to prevent or treat illnesses or disorders mediated by neurodegeneration. These formula (I) N-alkylglycine trimeres are also capable of preventing excitatory neuronal death caused by prolonged exposure of neuronal cultures to L-glutamine.

The capacity of formula (I) N-alkylglycine trimeres to prevent excitotoxic neurodegeneration can be demonstrated by means of a test that evaluates the efficiency and power of said N-alkylglycine trimeres abating neuronal death caused by prolonged exposure of primary cultures of rat cerebellum neurones to L-glutamine and glycine [see Example 1.2]. The neuroprotector mechanism implies, at least in part, the blocking of the glutamate ionotropic receptors, as is made manifest by the inhibition of the ionic current activated by the NMDA type of glutamatergic receptor agonist expressed in *X. laevis* ovocites (19,20). An important advantage of these biological tests is that they permit the search for neuroprotectors in functionally active systems, increasing the potentiality of its in vivo use.

Formula (I) N-alkylglycine trimeres can form part of diverse types of compositions for application in the body of mammals, preferably human beings. In this sense, the invention provides a composition that comprises at least one formula (I) N-alkylglycine trimere. In a particular embodiment, said composition is a pharmaceutical composition.

The Pharmaceutical composition provided by this invention comprises a therapeutically effective amount of at least one formula (I) N-alkylglycine trimere together with at least, one pharmaceutically acceptable excipient.

Formula (I) N-alkylglycine trimeres can be administered in order to treat the neurodegeneration, by any means that produces contact of the formula (I) N-alkylglycine trimeres with the site of action thereof in the body of a mammal, preferably a human being.

The amount of therapeutically efficient formula (I) N-alkylglycine trimeres that must be administered as well as its dose for treating a pathological condition mediated by neurodegeneration shall depend on numerous factors, including the age, condition of the patient, severity of the alteration or disorder, the route and frequency of the administration and the particular formula (I) N-alkylglycine trimere to be used.

The pharmaceutical composition provided by this invention may be presented under any administrational form, for example, solid or liquid, and may be administered in an, appropriate way, for example, orally, parenterally, rectal or topic, for which it shall include the necessary pharmaceutically acceptable excipients for the formulation of the desired administrational form. A revision of the different pharmaceutical forms of administration of the medicines and of the necessary excipients for their obtention may, for example, be found in the "Treaty of Galenic Pharmacy", C. Fauli i Trillo, 1993, Luzán 5, S.A. Ediciones, Madrid.

Consequently, an additional object of this invention is constituted by the employment of a formula (I) N-alkylglycine trimer in the elaboration of a medicine for the attenuation of the nervous activity of neurones involved in the neurodegeneration mediated by the application of exogenous chemical substances or by the endogenous liberation of chemical substances that cause excitotoxicity in the nervous system (excitotoxic or excitotoxine substances) or in the elaboration of a medicine that inhibits the ionic channels activated by exogenous chemical substances or by excitotoxines that lead to neurodegeneration.

More specifically, the invention refers to the use of formula (I) N-alkylglycine trimer in the elaboration of a medicine for the treatment of illnesses and pathological alterations mediated by the activity of the ionic channels of the L-glutamate ionotropic receptors, such as type NMDA receptors, for example, the neurodegeneration in response to a noxious stimulus.

More specifically, the invention refers to the use of a formula (I) N-alkylglycine trimer in the elaboration of a medicine for the treatment, slowing down, reduction, decrease and/or prevention of neurodegeneration, as well as the use of a formula (I) N-alkylglycine trimere in the elaboration of a medicine for the treatment of cerebral ischemia, cerebrovascular accident, migraine, depression, Huntington, Parkinson, Alzheimer, senile dementia, epilepsy and multiple and amiotropic sclerosis.

The invention additionally provides a method for the treatment in a patient of illnesses and pathological disorders mediated by the activity of the ionic channels and of the glutamate onotropic receptors, for example, the neurodegeneration mediated by glutamate ionotropic receptors in response to diverse noxious stimuli, for example, mechanical, chemical and thermal, that comprise the administration to said patient, suffering from said illness or pathological disorder, of a therapeutically effective amount of a formula (I) N-alkylglycine trimere, preferably, in the form of a pharmaceutical composition that contains it.

The amount of formula (I) N-alkylglycine trimeres to be administered shall depend on numerous factors, among which is to be found the degree of neurodegeneration produced by the excitotoxic aggressions and on the N-alkylglycine trimere to be used.

On the other hand, a fundamental requirement for the identification of bioactive molecules is to perform a test that permits the determination of its biological activity on the therapeutic targets. The inventors have developed a biological test that permits the evaluation of the power or the molecules that block the ionic current activated by agonist in *X. laevis* ovocites that express neuronal receptors, such as glutamatergical receptors (19, 20). An important advantage of this biological test is that it permits the search for antagonists in functionally active receptors, increasing the power of its use in vivo.

The receptor heterologous expression methods in *X. laevis* ovocites have been described in detail by Ferrer-Montiel and Montal (19).

The following examples serve to illustrate the nature of the present invention and shall not be considered in its limitative sense.

EXAMPLE 1

N-alkylglycine Trimeres Capable of Blocking the NMDA Receptor 1.1 N-alkylglycine Trimeres Synthesis The N-alkylglycine trimeres identified in Table 1 were synthesised by means of conventional methods of solidphase peptide synthesis (21). The trimeres were purified by means of high resolution liquid chromatography.

Table 1

Formula (I) N-alkylglycine Trimeres

[1]: [N-[3,3-diphenylpropyl]glycyl]-[N-[3-(N,N-diethylamine)propyl] glycyl]-N-[2-(methylcarbonylamine)ethyl]glycinamide;

[2]: [N-[3,3-diphenylpropyl]glycyl]-[N-[3-(N,N-diethylamine)propyl]glycyl]-N-[2-(2-pyridyl)ethyl]glycinamide;

[3]: [N-[3,3-diphenylpropyl]glycyl]-[N-[3-(N,N-diethylamine)propyl]glycyl]-N-[2-(N-imidazolyl)ethyl]glycinamide;

[4]: [N-[3,3-diphenylpropyl]glycyl]-[N-[3-(N,N-diethylamine)propyl]glycyl]-N-[3-(N,N-dimethylamine)propyl]glycinamide;

[5]: [N-[3,3-diphenylpropyl]glycyl]-[N-[3-N,N-diethylamine)propyl]glycyl]-N-[2-(methylcarbonylamine)ethyl]glycinamide;

[6]: [N-[3,3-diphenylpropyl]glycyl]-[N-[3-N,N-diethylamine)propyl]glycyl]-N-[2-(2-pyridyl)ethytl]glycinamide;

[7]: [N-[3,3-diphenylpropyl]glycyl]-[N-[3-N,N-diethylaminepropyl]glycyl]-N-[2-(N-imidazolyl)ethyl]glycinamide;

[8]: [N-[3,3-diphenylpropyl]glycyl]-[N-[3-(N,N-dimethylamine)propyl]glycyl]-N-[3-(N,N-dimethylamine)propyl]glycinamide;

[9a]: [N-[(R,S)-2-[2-(N-methyl)pyrrolidinyl]ethyl]glycyl]-[N-[3-(N,N-diethylamine)propyl]glycyl]-N-[2-(methylcarbonylamine)ethyl]glycinamide;

[9b]: [N-[(R)-2-[2-(N-methyl)pyrrolidinyl]ethyl]glycyl]-[N-[3-(N,N-diethylamine)propyl]glycyl]-N-[2-(methylcarbonylamine)ethyl]glycinamide;

[9c]: [N-[(S)-2-[2-(N-methyl)pyrrolidinyl]ethyl]glycyl]-[N-[3-(N,N-diethylamine)propyl]glycyl]-N-[2-(methylcarbonylamine)ethyl] glycinamide;

[10a]: [N-[(R,S)-2-[2-(N-methyl)pyrrolidinyl]ethyl]glycyl]-[N-[3-(N,N-diethylamine)propyl]glycyl]-N-[2-(2-pyridyl)ethyl]glycinamide;

[10b]: [N-[(R)-2-[2-(N-methyl)pyrrolidinyl]ethyl]glycyl]-[N-[3-(N,N-diethylamine)propyl]glycyl]-N-[2-(2-pyridyl)ethyl]glycinamide;

[10 c]: [N-[(S)-2-[2-(N-methyl)pyrrolidinyl]ethyl]glycyl]-[N-[3-(N,N-diethylamine)propyl]glycyl]-N-[2-(2-pyridyl)ethyl]glycinamide;

[11a]: [N-[(R,S)-2-[2-(N-methyl)pyrrolidinyl]ethyl]glycyl]-[N-[3-(N,N-diethylamine)propyl]glycyl]-N-[2-(N-imidazolyl))ethyl]glycinamide;

[11b]: [N-[(R)-2-(2-(N-methyl)pyrrolidinyl]ethyl]glycyl]-[N-[3-(N,N-diethylamine)propyl]glycyl]-N-[2-(N-imidazolyl)ethyl]glycinamide;

[11c]: [N-[(S)-2-(2-(N-methyl)pyrrolidinyl]ethyl]glycyl]-[N-[3-(N,N-diethylamine)propyl]glycyl]-N-[2-(N-imidazolyl)ethyl]glycinamide;

[12a]: [N-[(R,S)-2-(2-(N-methyl)pyrrolidinyl]ethyl]glycyl]-[N-[3-(N,N-diethylamine)propyl]glycyl]-N-[3-(N,N-dimethylamine)propyl]glycinamide;
[12b]: [N-[(R)-2-(2-(N-methyl)pyrrolidinyl]ethyl]glycyl]-[N-[3-(N,N-diethylamine)propyl]glycyl]-N-[3-(N,N-dimethylamine)propyl]glycinamide;
[12c]: [N-[(S)-2-(2-(N-methyl)pyrrolidinyl] ethyl]glycyl]-[N-[3-(N,N-diethylamine)propyl]glycyl]-N-[3-(N,N-dimethylamine)propyl]glycinamide;
[13a]: [N-[(R,S)-2-(2-(N-methyl)pyrrolidinyl]ethyl]glycyl]-[N-[3,3-diphenylpropyl]glycyl]-N-[2-(methylcarbonylamine)ethyl]glycinamide;
[13b]: [N-[(R)-2-(2-(N-methyl)pyrrolidinyl]ethyl]glycyl]-[N-[3,3-diphenylpropyl]glycyl]-N-[2-(methylcarbonylamine)ethyl]glycinamide;
[13c]: [N-[(S)-2-(2-(N-methyl)pyrrolidinyl]ethyl]glycyl]-[N-[3,3-diphenylpropyl]glycyl]-N-[2-(methylcarbonylamine)ethyl]glycinamide;
[14a]: [N-[(R,S)-2-(2-(N-methyl)pyrroildinyl]ethyl]glycyl]-[N-[3,3-diphenylpropyl]glycyl]-N-[2-(2-pyridyl)ethyl]glycinamide;
[14b]: [N-[(R)-2-(2-(N-methyl)pyrrolidinyl]ethyl]glycyl]-[N-[3,3-diphenylpropyl]glycyl]-N-[2-((2-pyridyl)ethyl]glycinamide;
[14c]: [N-[(S)-2-(2-(N-methyl)pyrrolidinyl]ethyl]glycyl]-[N-[3,3-diphenylpropyl]glycyl]-N-[2-(2-pyridyl)ethyl]glycinamide;
[15a]: [N-[(R,S)-2-(2-(N-methyl)pyrrolidinyl]ethyl]glycyl]-[N-[3,3-diphenylpropyl]glycyl]-N-[2-(N-imidazolyl)ethyl]glycinamide;
[15b]: [N-[(R)-2-(2-(N-methyl)pyrrolidinyl]ethyl]glycyl]-[N-[3,3-diphenylpropyl]glycyl]-N-[2-(N-imidazolyl)ethyl] glycinamide;
[15c]: [N-[(S)-2-(2-(N-methyl)pyrrolidinyl]ethyl]glycyl]-[N-[3,3-diphenylpropyl]glycyl]-N-[2-(N-imidazolyl)ethyl]glycinamide;
[16a]: [N-[(R,S)-2-(2-(N-methyl)pyrrolidinyl]ethyl]glycyl]-[N-[3,3-diphenylpropyl]glycyl]-N-[3-(N,N-dimethylamine)propyl]glycinamide;
[16b]: [N-[(R)-2-(2-(N-methyl)pyrrolidinyl]ethyl]glycyl]-[N-[3,3-diphenylpropyl]glycyl]-N-[3-(N,N-dimethylamine)propyl]glycinamide;
[16c]: [N-[(S)-2-(2-(N-methyl)pyrrolidinyl]ethyl]glycyl]-[N-[3,3-diphenylpropyl]glycyl]-N-[3-(N,N-dimethylamine)propyl]glycinamide;
[17a]: [N-(cyclopropyl)glycyl]-[N-(cyclopropyl)glycyl]-N-((R,S)-sec-butyl)glycinamide;
[17b]: [N-(cyclopropyl)glycyl]-[N-(cyclopropyl)glycyl]-N-((R)-sec-butyl)glycinamide;
[17c]: [N-(cyclopropyl)glycyl]-[N-(cyclopropyl)glycyl]-N-((S)-sec-butyl)glycinamide;
[18]: [N-(cyclopropyl)glycyl]-[N-(cyclopropyl)glycyl]-N-(phenethyl)glycinamide;
[19]: [N-(cyclopropyl)glycyl]-[N-(cyclopropyl)glycyl]-N-[2-(4-aminosulfonylphenyl)ethyl]glycinamide;
[20a]: [N-(cyclopropyl)glycyl]-][N-[2-(N-morpholine)ethyl]glycyl]-N-((R,S)-sec-butyl)glycinamide;
[20b]: [N-(cyclopropyl)glycyl]-][N-[2-(N-morpholine)ethyl]glycyl]-N-((R)-sec-butyl)glycinamide;
[20c]: [N-(cyclopropyl)glycyl]-[N-[2-(N-morpholine)ethyl]glycyl]-N-((S)-sec-butyl)glycinamide;
[21]: [N-(cyclopropyl)glycyl]-][N-[2-(N-morpholine)ethyl]glycyl]-N-(phenethyl)glycinamide;
[22]: [N-(cyclopropyl)glycyl]-[N-[2-(N-morpholine)ethyl]glycyl]-N-[2-(4-aminosulfonylphenyl)ethyl]glycinamide
[23a]: [N-[2-(N-pyrrolidinyl)ethyl]glycyl]-[N-(cyclopropyl)glycyl]-N-((R,S)-sec-butyl)glycinamide;
[23b]: [N-[2-(N-pyrrolidinyl)ethyl]glycyl]-[N-(cyclopropyl)glycyl]-N-((R)-sec-butyl)glycinamide;
[23c]: [N-[2-(N-pyrrolidinyl)ethyl]glycyl]-[N-(cyclopropyl)glycyl]-N-((S)-sec-butyl)glycinamide;
[24]: [N-[2-(N-pyrrolidinyl)ethyl]glycyl]-[N-(cyclopropyl)glycyl]-N-(phenethyl)glycinamide
[25]: [N-[2-(N-pyrrolidinyl)ethyl]glycyl]-[N-(cyclopropyl)glycyl]-N-[2-(4-aminosulfonylphenyl)ethyl]glycinamide;
[26a]: [N-[2-(N-pyrrolidinyl)ethyl]glycyl]-[N-[2-(N-morpholine)ethyl]glycyl]-N-((R,S)-sec-butyl)glycinamide;
[26b]: [N-[2-(N-pyrrolidinyl)ethyl]glycyl]-[N-[2-(N-morpholine)ethyl]glycyl]-N-((R)-sec-butyl)glycinamide;
[26c]: [N-[2-(N-pyrrolidinyl)ethyl]glycyl]-[N-[2-(N-morpholine)ethyl]glycyl]-N-((S)-sec-butyl)glycinamide;
[27]: [N-[2-(N-pyrrolidinyl)ethyl]glycyl]-[N-[2-(N-morpholine)ethyl]glycyl]-N-(phenethyl)glycinamide and
[28]: [N-[2-(N-pyrrolidinyl)ethyl]glycyl]-[N-[2-(N-morpholine)ethyl]glycyl]-N-(2-(4-aminosulfonylphenyl)ethyl)glycinamide 1.2. Evaluation of the Biological Activity Two complementary biological tests were used in order to evaluate the biological activity of the N-alkylglycine trimeres obtained in Example 1.1. The first evaluates the efficiency and power with which said compounds block the ionic current activated by agonists in $X.$ $laevis$ ovocites that express the NMDA receptor. The second, determines the neuroprotector efficiency of the N-alklyglycine trimeres in primary cultures of neurones subjected to an excitotoxic aggression, such as prolonged exposure to L-glutamate and glycine.

The heterological expression of receptors in $X.$ $laevis$ ovocites can be performed according to the procedure described by Ferrer-Montiel and Montal (19). Briefly, the $X.$ $laevis$ ovocites of adult frogs are gathered, manipulated and injected with cDNA that codes NR1 and NR2A sub-unities of NMDA receptor (5,20). The ionic currents activated by the L-glutamate agonist in the presence of the glycine coagonist are recorded with the maintenance of the constant voltage method with two microelectrodes (two-microelectrode voltage lamp) (19, 20). The ovocites hat express the receptor are transferred to the recording chamber and are perfused using an 8 output perfusion system. The agonist and the coagonist, both in the absence and in the presence of the N-alkylglycine trimere to be tested, are dissolved in a Ringer buffer (Hepes 10 mM pH 7.4 NaCl 100 mM, $BaCl_2$ 2.0 mM, RCl 3.0 mM) supplemented with 100 $\mu$m fluphenamic acid (20). This buffered solution is used to minimize the contribution of the chloride endogenous ionic channel activated by calcium to the ionic current of the glutamatergic receptor (19, 20). The transmembrane voltage is maintained constant at −80 mV, and the ionic currents are activated by applying pulses of the L-glutamate/glycine solution (100 $\mu$M/20 $\mu$M) in the presence or absence of growing concentrations of the N-alkylglycine trimeres to be tested. The inhibiting activity is detected by measuring the ionic current activated by the agonist in the presence and absence of the N-alkylglycine trimeres.

The power and efficiency of the inhibiting activity of the N-alkylglycine trimeres is determined by means of the obtention of dose-response curves. For this, the magnitude of the ionic channel blocking activated by L-glutamate/glycine in ovocites that express the NMDA receptor in the presence of growing concentrations of the N-alkylglycine trimere is examined. The ratio of ionic current intensities in the presence and absence of said N-alkylglycine trimere is used to obtain the dose-response curves (19, 20). These graphs meet logarithmic functions to determine the maximum blockage power) and the antagonist concentration that is produced by half the maximum blockage ($IC_{50}$, efficiency)

The results obtained showed that all the tested N-alkylglycine trimeres blocked the ionic channel activity that is characteristic of the NMDA receptor expressed in *X. laevis* of frog ovocites. The N-alkylglycine trimere concentrations that inhibited half the NMDA receptor response ($IC_{50}$) activated by L-glutamate/glycine at a concentration of 100 $\mu$M/20 $\mu$M, oscillated between 0.1 $\mu$M and 100 $\mu$M for the different N-alkylglycine trimeres tested (Table 1). Thus, for example, the $IC_{50}$ of the N-alkylglycine trimere identified as compound [2] is of approximately 2 $\mu$M and of approximately 10 $\mu$M for the N-alkylglycine trimere identified as compound [3]. The rest of the compounds showed $IC_{50}$ values comprised between 10 and 100 $\mu$M.

Additionally, it was observed that the N-alkylglycine trimeres tested did not behave as competitive antagonists of the natural agonist.

It was also observed that the N-alkylglycine trimeres tested protected primary neuronal cultures coming from the cerebellum of rats pre-exposed to 10 $\mu$M glycine versus the prolonged exposure ($\geq$3 h) of L-glutamate or N-methyl-D-aspartate at a concentration of 1 ml. The test consists of extracting the cerebellar neurones of baby rats, 7–8 days old, cultivating them in plates in a culture medium supplemented with bovine foetal serum (22). After 13–19 days under culture, the excitotoxic aggression with L-glutamate is performed, monitoring the neuronal death in the absence and presence of the N-alkylglycine trimeres 24 hours post-aggression using two fluorescent dyes: the fluorescent diacetate that indicates the number of viable cells, and the propydium iodine that informs of the number of dead cells (23). As an example, the N-alkylglycine trimere identified as compound [1] decreased a 95% of the neuronal death at a concentration of 30 $\mu$g/ml; compound [5] an 85% at 30 $\mu$g/ml; compound [23a] a 57% at a concentration of 50 $\mu$g/ml, and compound [24] a 60% at 50 $\mu$g/ml. The rest of the N-alkylglycine trimeres tested, showed neuronal protection efficiencies that oscillated between 37% and 96%.

Additionally, it was observed that the N-alkylglycine trimeres tested showed a glutamate neurotoxicity protecting effect in animal models. A neurotoxicity model was used on mice induced by the injection of high doses of ammonium, the result of which is the death of the animal due to the hyperactivation of the NMDA receptor. The test consists in the intraperitoneal injection in mice of an amount of N-alkylglycine trimere of 0.05–0.1 mg/g, followed, after 10 minutes, with an injection of 12 mmol/kg of ammonium acetate. After 24 hours post-injection, the number of dead mice was determined. The N-alkylglycine trimere identified as compound [24] protected 82% of the mice, whilst the N-alkylglycine trimere identified as compound [23a] protected 100% of the animals.

On the other hand, due to the fact that some formula I N-alkylglycine trimeres may be presented as stereoisomers, the possibility that the neuroprotector activity of the racemic mixture preferably corresponded to one of the isomers, was evaluated. For this, the neuroprotector activity of the enantiomers identified as [23b] and [23c] was evaluated, (see Table 1) in primary cultures of cerebellar neurons exposed to excitotoxic aggression, such as the incubation with L-glutamate 1 mM comparing it with the neuroprotector activity of a racemic mixture of said enantiomers. The results obtained were similar in both cases and showed that both enantiomers are neuroprotectors with equal power. Likewise, said power was similar to the one presented by the racemic mixture.

Given the role of the NMDA receptor in the excitatory synaptic transmission and in the etiology of the numerous neurodegenerative illnesses, a consequence of the blocker activity of the N-alkylglycine trimeres provided by this invention is their use as useful neuroprotecters to decrease or reduce the neuronal death caused by excitotoxic aggression, such as cerebral ischemia, the neurodegeneration mediated by hyperammonemia, Alzheimer dementia, epilepsy, etc.

Bibliography

1. Olney, J. W. (1990). Excitotoxic amino acid and neuropsychiatric disorders. *Annu. Rev. Pharmacol. Toxicol.* 30, 47–71.
2. Lipton, S. A. and Rosenburg, P. A. (1994). Excitatory amino acids as a final common pathway for neurologic disorders. *New Engl. J. Med.* 330, 613–622.
3. Chol, D. W., and Rothmann, S. M. (1990). The role of glutamate neurotoxicity in hypoxic ischemic neuronal death. *Annu. Rev. Neurosci.* 13, 171–182
4. Collingridge, G. L. and Lester, R. A. J. (1989). Excitatory amino acid receptors in the vertebrate central nervous system. *Phamacol. Rev.* 40, 143–210.
5. Choi, D. W. (1994). Calcium and excitotoxic neuronal injury. *Ann. N.Y. Acad. Sci* 747, 162–171.
6. Siesjö, B. K. (1994). Calcium-mediated processes in neuronal degeneration. *Ann. N.Y. Acad. Sci* 747, 140–161.
7. Lipton, S. A. (1994). AIDS-related dementia and calcium homeostasis, *Ann. N.Y. Acad. Sci* 747, 205–224.
8. Montoliu, C., Llansola, M. Kosenko, E., Corbalán, R., Pelipo, V. (1999). Role of cyclic GMP in glutamate neurotoxicity in primary cultures of cerebellar neurons. *Neurophamacology* 38, 1883–1891.
9. Kornhuber, J. and Quack, G. (1995). Cerebrospinal fluid and serum concentrations of the N-methyl-D-asparate (NMDA) receptor antagonist memantine in man. *Neurosci. Lett.* 195, 137–139.
10. Nakanishi, S. and Masu, M. (1994). Molecular diversity and functions of glutamate receptors (1994) *Annu. Rev. Biophys. Biomol. Struc.* 23, 319–348.
11. Herrling, P L. (1994). Clinical implications of NMDA receptor. *In the NMDA receptor*, Eds G. L. Collingridge and J. C. Watkins, $2^{nd}$ Ed. 376–394.
12. Lipton, S. A. (1993) Prospects for clinically tolerated NMDA antagonists: open channel blockers and alternative redox states of nitric oxide. *Trends neurosci.* 16, 527–532.
13. Müller, W. E., Mutschlèr, E. and Riederer, P. (1995). Non-competitive NMDA receptor antagonists with fast open channel blocking kinetics and strong voltage dependency as potential therapeutic agents for Alzheimer's. *Pharmcopsychiat* 28, 113–124.
14. Iversen, L. L and Kemp, J. A (1994). Non-competitive NMDA antagonists as drugs. *In: the NMDA receptor*. Eds. G. L. Collingridge and J. C. Watkins. $2^{nd}$ Ed. 469–486.
15. Miñana, M. D., Hermenegildo, C., Llansola, M., Montoliu, C., Grisolia, S. and Felipo, V. (1996) Carnitine and choline derivatives containing a trimethylamine group prevent amonia toxicity in mice and glutamate toxicity in primary cultures or neurones. *J. Pharmacol. Exp. Ther.* 279, 194–199.
16. Koek, W., Woods, J. H. and Winger, G. D. (1988). MK-801, a proposed noncompetitive antagonist of excitatory amino acid neurotransmission, produces phencyclidine-like behavioral effects in pigeons, rats and rhesus monkeys. *J. Pharmacol. Exp. Ther.* 245, 969–974.
17. Choi, D. W. (1987) Dextrorphan and dextromethorphan attenuate glutamate neurotoxicity. *Brain res.* 403, 333–336.
18. Seif el Nasr, M., Peruche, B., Rossberg, C., Mennel, H.-D. and Krieglstein, J. (1990). Neuroprotective effect of memantine demonstrated in vivo and in vitro. *Eur. J. Pharmacol.* 185, 19–24.
19. Ferrer-Montiel, A. V. and Montal, N. (1994). Structure-function relations in ligand-gated ion channels: Reconstitution in lipid bilayers arid heterologous expression in *Xenopus occytes. Methods: a Companion to Methods in Enzymology* 6, 60–69.
20. Ferrer-Montiel, A. V., Sun, W. and Montal, M. (1995). Molecular design of the NMDA receptor binding site for PCP and MK-801. *Proc. Natl. Acad. Sci. USA.* 92, 8021–8025.
21. (A) Suckermann, R. N., Herr, J. M., Kent, S. B. H., Moos, W. H. (1992). Efficient method for the preparation of peptoids [oligo(N-substituted glycines)] by submonomer solid-phase synthesis. *J. Am. Chem. Soc.* 14, 10646–10647. (B) Figliozzi, G. M., Goldsmith, R., Ng., S. C., Banville, S. C., Zuckermann, R. N. (1996) Synthesis of N-substituted glycine peptoid libraries. *Method Enaymol.* 267, 437–447.
22. Miñana M. D., Montoliu, C., Llansola, M. Grisolla, S., Felipo. V. Nicotine prevents glutamate-induced proteolysis of the microtubule-associated protein MAP-2 and glutamate neurotoxicity in primary cultures of cerebellar neurons. *Neuropharmacology* 37, 847–857.
23. Maracaida, G., Miñana, M. D., Burgal, M., Grisolia, S. and Felipo, V. (1995) Ammonia prevents activation of NMDA receptors in rat cerebellar neuronal cultures. *Eur. J. Neurosci.* 7, 2389–2396.

What is claimed is:
1. A N-alkylglycine trimere of general formula (I)

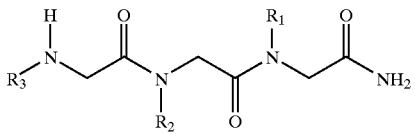

wherein $R_1$, $R_2$ and $R_3$, are the same or different and are independently selected from the group consisting of cyclopropyl, sec-butyl, 2-methoxyethyl, 3-methylbutyl, cylohexyl, 2-(N-pyrrolidinyl)ethyl, 2-(methylcarbonylamine) ethyl, 3-(2-oxo-N-pyrrolidinyl)propyl, 2-(2-pyridyl)ethyl, 2-phenylethyl, 1-(2-tetrahydrofuryl) methyl, 2-(N-imidazolyl)ethyl, 2-(4-methoxyphenyl)ethyl, 2-(3,4-dimethoxyphenyl)ethyl, 2-(2,4-dichiorophenyl)ethyl, 2-[2-(N-methyl)pyrrolidinyl]ethyl, 2-(4-aminosulphonylphenyl)ethyl, 2-(morpholine)ethyl, 3-(N,N-diethylamine)propyl, 3,3-diphenylpropyl, 3-(N,N-dimethylamine)propyl and 2-(N,N-diethylamine)ethyl,
    a non-racemic stereoisomeric form or racemic mixture of said N-alkylglycine trimere, or
    a pharmaceutically acceptable salt of said N-alkylglycine trimere.
2. A N-alkylglycine trimere, stereoisomeric form, racemic mixture or salt according to claim 1, wherein $R_1$ is sec-butyl, 2-phenylethyl, 2-(methylcarbonylamine)ethyl, 3-(N,N-dimethylamino)propyl, or 2-(N-imidazolyl)ethyl.

3. A N-alkylglycine trimere, stereoisomeric form, racemic mixture or salt according to claim 1, wherein $R_2$ is cydopropyl, 3-(N,N-diethylamino)propyl, 2-morpholine)ethyl or 3,3-diphenylpropyl.
4. A N-alkylglycine triniere, stereoisomeric form, racemic mixture or salt according to claim 1, wherein $R_3$ is 2-(N-pyrrolidinyl)ethyl, cyclopropyl, 3,3-diphenylpropyl or 2-[2-(N-methyl)pyrrolidinyl]ethyl.
5. A N-alkylglycine trimere, stereoisomeric form, racemic mixture or salt according to claim 1, wherein the N-alkylglycine trimere is selected from the group consisting of:
[1]: [N-[3,3-diphenylpropyl]glycyl]-[N-[3-(N,N-diethylamine)propyl]glycyl)-N-[2-(methylcarbonylamine) ethyl]glycinamide;
[2]: [N-[3,3-diphenylpropyl]glycyl]-[N-[3-(N,N-diethylamine)propyl]glycyl]-N-[2-(2-pyridyl)ethyl]glycinamide;
[3]: [N-[3,3-diphenylpropyl]glycyl]-[N-3-(N,N-diethylamine)propyl]glycyl]-N-[2-(N-imidazolyl)ethyl]glycinamide;
[4]: N-[3,3diphenylpropyl]glycyl]-[N-[3-(N,N-diethylamine)propyl]glycyl]-[N-[3-(N,N-dimethylamine)propyl]glycinamide;
[5]: [N-[3,3-diphenylpropyl]glycyl]-[[N-[3,3-diphenylpropyl]glycyl]-N-[2-(methylcarbonylamine)ethyl]glycinamide;
[6]: [N-[3,3-diphenylpropyl]glycyl]-[N-[3,3-diphenylpropyl]glycyl]-N-[2-(2-pyridyl)ethyl]glycinamide;
[7]: [N-[3,3-diphenylpropyl]glycyl]-[N-[3,3-diphenylpropyl]glycyl]N-[2-(N-imidazolyl)ethyl]glycinamide;
[8]: [N-[3,3-diphenylpropyl]glycyl]-[N-[3,3-diphenyl propyl]glycyl]-N-[3-(N,N-dimethylamine)propyl]glycinamide;
[9a]: [N-[(R, S)-2-[2-(N-methyl)pyrrolidinyl]ethyl]glycyl]-[N-[3-(N,N-diethylamine)propyl]glycyl]-N-[2-(methylcarbonylamine)ethyl]glycinamide;
[9b]: [N-[(R)-2-[2-(N-methyl)pyrrolidinyl]ethyl]glycyl]-[N-[3-(N,N-diethylamine)propyl]glycyl]-N-[2-(methylcarbonylamine)ethyl]glycinamide;
[9c]: [N-[(S)-2-[2-(N-methyl)pyrrolidinyl]ethyl]glycyl]-[N-[3-(N,N-diethylamine)propyl]glycyl]-N-[2-(methylcarbonylamine)ethyl]glycinamide;
[10a]: [N-[(R, S)-2-[2-(N-methyl)pyrrolidinyl]ethyl]glycyl]-[N-]3-(N,N-diethylamine)propyl]glycyl]-N-[2-(2-pyridyl)ethyl]glycinamide;
[10b]: [N-[(R)-2-[2-(N-methyl)pyrrolidinyl]ethyl]glycyl]-[N-[3-(N,N-diethylamine)propyl]glycyl]-N-[2-(2-pyridyl)ethyl]glycinamide;
[10c]: [N-(S)-2-[2-(N-methyl)pyrrolidinyl]ethyl]glycyl]-[N-[3-(N,N-diethylamine)propyl]glycyl]-N-[2-(2-pyridyl)ethyl]glycinamide;
[11a] [N-[(R, S)-2-[2-(N-methyl)pyrrolidinyl]ethyl]glycyl]-[N-[3-(N,N-diethylamine)propyl]glycyl]-N-[2-(N-imidazolyl)ethyl]glycinamide;
[11b] [N-[(R)-2-[2-(N-methyl)pyrrolidinyl]ethyl]glycyl]-[N-[3-(N,N-diethylamine)propyl]glycyl]-N-[2-(N-imidazolyl)ethyl]glycinamide;
[11c]: [N-[(S)-2-[2-(N-methyl)pyrrolidinyl]ethyl]glycyl]-[N-[3-(N,N-diethylamine)propyl]glycyl]-N-[2-(N-imidazolyl)ethyl]glycinamide;
[12a]: [N-[(R, S)-2-[2-(N-methyl)pyrrolidinyl]ethyl]glycyl]-[N-[3-(N,N-diethylamine)propyl]glycyl]-N-[3-(N,N-dimethylamine)propyl]glycinamide;
[12b]: [N-[(R)-2-[2-(N-methyl)pyrrolidinyl]ethyl]glycyl]-[N-[3-(N,N-diethylamine)propyl]glycyl]-N-[3-(N,N-dimethylamine)propyl]glycinamide;

[12c]: [N-[(S)-2-[2-(N-methyl)pyrrolidinyl]ethyl]glycyl]-[N-[3-(N,N-diethylamine)propyl]glycyl]-N-[3-(N,N-dimethylamine)propyl]glycinamide;

[13a]: [N-[(R, S)-2-[2-(N-methyl)pyrrolidinyl]ethyl]glycyl]-[N-[3,3-diphenylpropyl]glycyl]-N-[2-(methylcarbonylamine)ethyl]glycinamide;

[13b]: [N-[(R)-2-[2-(N-methyl)pyrrolidinyl]ethyl]glycyl]-[N-[3,3-diphenylpropyl]glycyl]-N-[2-(methylcarbonylamine)ethyl]glycinamide;

[13c]: [N-[(S)-2-[2-(N-methyl)pyrrolidinyl]ethyl]glycyl]-[N-[3,3-diphenylpropyl]glycyl]-N-[2-(methylcarbonylamine)ethyl]glycinamide;

[14a]: [N-[(R, S)-2-[2-(N-methyl)pyrrolidinyl]ethyl]glycyl]-[N-[3,3-diphenylpropyl]glycyl]-N-[2-(2-pyridyl)ethyl]glycinamide;

[14b]: [N-[(R)-2-[2-(N-methyl)pyrrolidinyl]ethyl]glycyl]-[N-[3,3-diphenylpropyl]glycyl]-N-[2-(2-pyridyl)ethyl]glycinamide;

[14c]: [N-[(S)-2-[2-(N-methyl)pyrrolidinyl]ethyl]glycyl]-[N-[3,3-diphenylpropyl]glycyl]-N-[2-(2-pyridyl)ethyl]glycinamide;

[15a]: [N-[(R, S)-2-[2-(N-methyl)pyrrolidinyl]ethyl]glycyl]-[N-[3,3-diphenylpropyl]glycyl]-N-[2-(N-imidazolyl)ethyl]glycinamide;

[15b]: [N-[(R)-2-[2-(N-methyl)pyrrolidinyl]ethyl]glycyl]-[N-[3,3-diphenylpropyl]glycyl]-N-[2-(N-imidazolyl)ethyl]glycinamide;

[15c]: [N-[(S)-2-[2-(N-methyl)pyrrolidinyl]ethyl]glycyl]-[N-[3,3-diphenylpropyl]glycyl]-N-[2-(N-imidazolyl)ethyl]glycinamide;

[16a]: [N-[(R, S)-2-[2-(N-methyl)pyrrolidinyl]ethyl]glycyl]-[N-[3,3-diphenylpropyl]glycyl]-N-[3-(N,N-dimethylamine)propyl]glycinamide;

[16b]: [N-[(R)-2-[2-(N-methyl)pyrrolidinyl]ethyl]glycyl]-[N-[3,3-diphenylpropyl]glycyl]-N-[3-(N,N-dimethylamine)propyl]glycinamide;

[16c]: [N-[(S)-2-[2-(N-methyl)pyrrolidinyl]ethyl]glycyl]-[N-[3,3-diphenylpropyl]glycyl]-N-[3-(N,N-dimethylamine)propyl]glycinamide;

[17a]: [N-(cyclopropyl)glycyl]-[N-(cyclopropyl)glycyl]-N-((R, S)-sec-butyl)glycinamide;

[17b]: [N-(cyclopropyl)glycyl]-[N-(cyclopropyl)glycyl]-N-((R)-sec-butyl)glycinamide;

[17c]: [N-(cyclopropyl)glycyl]-[N-(cyclopropyl)glycyl]-N-((S)-sec-butyl)glycinamide;

[18]: [N-(cyclopropyl)glycyl]-[N-(cyclopropyl)glycyl]-N-(2-phenethyl)glycinamide;

[19]: [N-(cyclopropyl)glycyl]-[N-(cyclopropyl)glycyl]-N-[2-(4-aminosulfonylphenyl)ethyl]glycinamide;

[20a]: [N-(cyclopropyl)glycyl]-[N-[2-(N-morpholine)ethyl]glycyl]-N-((R, S)-sec-butyl)glycinamide;

[20b]: [N-(cyclopropyl)glycyl]-[N-[2-(N-morpholine)ethyl]glycyl]-N-((R)-sec-butyl)glycinamide;

[20c]: [N-(cyclopropyl)glycyl]-[N-[2-(N-morpholine)ethyl]glycyl]-N-((S)-sec-butyl)glycinamide;

[21]: [N-(cyclopropyl)glycyl]-[N-[2-(N-morpholine)ethyl]glycyl]-N-(2-phenethyl)glycinamide;

[22]: [N-(cyclopropyl)glycyl]-[N-[2-(N-morpholine)ethyl]glycyl]-N-[2-(4-aminosulfonylphenyl)ethyl]glycinamide;

[23a]: [N-[2-(N-pyrrolidinyl)ethyl]glycyl]-[N-(cyclopropyl)glycyl]-N-((R,S)-sec-butyl)glycinamide;

[23b]: [N-[2-(N-pyrrolidinyl)ethyl]glycyl]-[N-(cyclopropyl)glycyl]-N-((R)-sec-butyl)glycinamide;

[23c]: [N-[2-(N-pyrrolidinyl)ethyl]glycyl]-[N-(cyclopropyl)glycyl]-N-((S)-sec-butyl)glycinamide;

[24]: [N-[2-(N-pyrrolidinyl)ethyl]glycyl]-[N-(cyclopropyl)glycyl]-N-(2-phenethyl)glycinamide;

[25]: [N-[2-(N-pyrrolidinyl)ethyl]glycyl]-[N-(cyclopropyl)glycyl]-N-[2-(4-aminosulfonylphenyl)ethyl]glycinamide;

[26a]: [N-[2-(N-pyrrolidinyl)ethyl]glycyl]-[N-[2-(N-morpholine)ethyl]glycyl]-N-((R, S)-sec-butyl)glycinamide;

[26b]: [N-[2-(N-pyrrolidinyl)ethyl]glycyl]-[N-[2-(N-morpholine)ethyl]glycyl]-N-((R)-sec-butyl)glycinamide;

[26c]: [N-[2-(N-pyrrolidinyl)ethyl]glycyl]-[N-[2-(N-morpholine)ethyl]glycyl]-N-((S)-sec-butyl)glycinamide;

[27]: [N-[2-(N-pyrrolidinyl)ethyl]glycyl]-[N-[2-(N-morpholine)ethyl]glycyl]-N-(2-phenethyl)glycinamide; and

[28]: [N-[2-(N-pyrrolidinyl)ethyl]glycyl]-[N-[2-(N-morpholine)ethyl]glycyl]-N-(2-(4-aminosulfonylphenyl)ethyl)glycinamide.

6. A pharmaceutical composition for the prevention or treatment of neurodegenerative disorders comprising a therapeutically effective amount of at least one formula (I) N-alkylglycine trimere according to any one of claims 1 to 5 and at least one pharmaceuticaly acceptable excipient.

7. A method for treating, slowing down, reducing, decreasing and/or preventing neurodegeneration in a subject, the method comprising administering to the subject an effective amount of a N-alkylglycine trimere of formula (I).

8. A method according to claim 7 wherein said neurodegeneration is mediated by excitotoxicity in the nervous system attributable to the application of exogenous chemical substances, or to endogenous liberation of chemical substances.

9. A method according to claim 7 wherein said neurodegeneration is a consequence of pathological ion channel activity attributable to the application of exogenous chemical substances, or to endogenous liberation of chemical substances.

10. A method according to claim 7 wherein said neurodegeneration is caused by pathological L-glutamate ionotropic receptor activity attributable to the application of exogenous chemical substances, or to endogenous liberation of chemical substances.

11. A method according to claim 7 wherein said neurodegeneration is selected from neurodegeneration consequent to cerebral ischernia, cerebrovascular accident, migraine, depression, Huntington's disease, Parkinson's disease, Alzheimer's disease, senile dementia, epilepsy, multiple sclerosis or amyotrophic sclerosis.

* * * * *